United States Patent [19]

Martin

[11] Patent Number: 4,698,019

[45] Date of Patent: Oct. 6, 1987

[54] DENTAL INSTRUMENT

[76] Inventor: James A. Martin, Wieand Rd., P.O. Box 77, Milford Square, Pa. 18935

[21] Appl. No.: 831,321

[22] Filed: Feb. 20, 1986

Related U.S. Application Data

[63] Continuation-in-part of Ser. No. 663,481, Oct. 22, 1984, abandoned.

[51] Int. Cl.4 ............................................... A61C 3/02
[52] U.S. Cl. ................................................... 433/144
[58] Field of Search ................ 433/141, 142, 143, 144

[56] References Cited

PUBLICATIONS

Thompson Dental Publication, 1201 So., 6th St. West Missoula MT 59881, May 1984 pp. 1 and 10.

Primary Examiner—Robert Peshock
Attorney, Agent, or Firm—Joseph W. Molasky & Assoc.

[57] ABSTRACT

A dental instrument having an elongated handle with blades mounted on opposite ends. Each blade is comprised of three cutting edges and a finely honed tip which may be used to carve, clean and restore teeth and refine dental casts. A uniquely configured shank joins said blade to said handle and provides an improved means for manipulating the blades so that improved surgical and laboratory restorations can be effected.

7 Claims, 5 Drawing Figures

DENTAL INSTRUMENT

This is a Continuation-in-part of applicant's copending application filed 10/22/84 Ser. No. 663,481 now abandoned.

This invention relates to a dental instrument having utility in the cleaning, carving and finishing of teeth and dental casts.

This invention constitutes a significant contribution to the art of dental technology because it allows the technician to make dental repairs and restorations with an ease not heretofore possible.

The instrument of this invention is a true carver because it possesses a plurality of finely honed cutting edges which can be used to scrape tartar or plaque from the external surfaces of teeth as well as deposits from the roots of teeth.

This instrument also enables technicians to remove air bubbles, interference and fissures from dental casts. In addition, it is designed to remove a model cast of a gum area and thus provide a replica of the patient's dental anatomy and tooth structure so that a dental prosthetic appliance can be fabricated.

The cutting edges terminate in a finely pointed tip which can be inserted between the teeth to remove tartar, calculus or stains which would otherwise be difficult or impossible to reach. The handle of this instrument is double-ended with identical blades on opposite ends so that an alternate cutting edge will be available in the event that one becomes damaged or dulled.

A pair of obliquely configured shank segments join said blades to said handle and allow the operator to convert exerted pressure into an improved carving operation. The shank segments obtrude from the shaft at an angle which diverges from the handle axis and the divergence is such that it forms a slightly spiraled contoured segment for receiving the operator's middle finger. This contoured segment or concavity provides a fulcrum point upon which the instrument turns when pressure is exerted and it is located so closely adjacent to the cutting edge that it permits the operator to facilely manipulate the blades and tip and perform the restoration process with remarkable ease.

BACKGROUND OF THE INVENTION

Anatomically, every tooth contains depressions, elevations and projections but every tooth is also distinct from another.

Most dental instruments are designed to conform only to the anatomy of a particular tooth while others provide means for intermarginal contouring between adjacent teeth; therefore, in performing dental restorations a plurality of instruments are usually provided so that their cutting edges can be matched with the tooth which is sought to be contoured. However, there are no instruments presently available which can be classified as true carvers and none possess the variety of cutting edges needed to complete an entire restoration.

Most cast-carving instruments possess smooth, rounded features which have the effect of scraping tooth surfaces. Others such as dental curettes, are equipped with blades which are ground at substantially right angles so as to provide the user with means for removing calcareous deposits from tooth roots. The blades in these latter instruments are ground at about 90 degrees to the axis but more acute angles of 45 degrees or less are also available. In addition, most instruments are equipped with blades in which the shank is spiraled so that the user can more easily insert the instrument between the patient's teeth.

Unfortunately, these instruments provide only one or two cutting edges at each end of the handle. Moreover, the shank portion to which they are attached is generally of extreme length and the cutting edges either do not conform to the tooth surface or they are arranged in such manner that it is difficult to manipulate the instrument.

THE INVENTION

The instrument of this invention overcomes the difficulties associated with known devices.

One object is to provide a dental instrument with a relatively short shank so that the tooth or dental cast which is sought to be carved or restored can be brought closer to the handle and thus provide the operator with greater control.

Another object is to provide a dental instrument in which the shank is obliquely disposed with respect to the handle so that its cutting edges and fine tip can be inserted into depressions and bifurcations without lacerating surrounding tissue.

Still another object is to provide a dental instrument in which the shank portion is characterized by a concavity into which the operator may impress his middle finger so as to exert maximum pressure and more easily manipulate the cutting blades.

Another object is to provide a dental instrument in which the axis of the handle extends on a line which passes adjacent to the tip, so that, in hand, at its fulcrum point, the instrument has unique and extraordinary balance.

Still another object is to provide a dental instrument in which each cutting blade contains three cutting edges, each of which can be used as a carver.

Structurally, the device of this invention is a rigid instrument which consists of the following:

(1) an elongated handle which can be held and manipulated by the user;

(2) an abbreviated and obliquely curved first shank which is secured to one end of said handle, the inside segment of which terminates in a first blade comprised of three linear cutting edges;

(3) an abbreviated and obliquely curved second shank which is secured to the opposite end of said handle, the inside segment of which terminates in a second blade comprised of three linear cutting edges;

(4) said first and second blades being comprised of two surfaces which form an angle of from about 40 to 50 degrees, each surface having a linear edge suitable for dental carving and leading to a pointed tip; and (5) said first and second blades having a third cutting edge at the point of curvature on the inside portion of said shank immediately above said surfaces.

A novel aspect of this invention resides in the oblique configuration of the shank segment. The shank diverges from the longitudinal axis of the handle and forms midway of the blade a concave segment which is contoured to receive the operator's middle finger. This feature and the abbreviated nature of the shank allow the operator to exert maximum pressure at the concavity immediately adjacent to the cutting edge so that the blade can be manipulated in a facile and efficient manner. The axis of the handle extends beyond the concavity on a line adjacent to the tip of the blade to provide balance as a result of which the user may exert maximum blade pressure on the tooth without slippage or a turning away of the instrument.

As a result, it is now possible to remove from a model cast the excess of stone or plaster and there may also be cut away with ease the mass of subgingival debris and foreign deposits which accummulate around the roots of teeth and contribute to periodontal disease. Accummulations such as these become calcified in time and only their removal can return the teeth and tissue to a healthy state.

Another point of novelty is the presence of three cutting edges on opposite ends of the instrument.

Although double-ended instruments with two blades are commonly used in dental surgery they generally possess only two cutting edges on each end.

The present invention improves upon known devices by providing on each end of an elongated shaft or handle a single blade which possesses two opposed and linear cutting edges which lie on the same plane and a third linear concave cutting edge which lies approximately equidistant of the opposed cutting edges on an inclined plane.

The instrument of this invention may be formed from any suitably rigid material as, for example, a hard metal such as steel or a durable plastic, but stainless steel is preferred.

The elongated handle, shank and blade segments are integrally formed from a single source material but it will be appreciated by those skilled in the art that they may also be fabricated as discrete elements which can be joined by means which are well known in the art to form a unitary tool.

These and other objects of the invention are illustrated by the accompanying Drawings. These Drawings show the handle with a milled design, but this is for illustration only and it may be replaced by any desired pattern without departing from the spirit or scope of this invention.

THE DRAWINGS

THE EMBODIMENTS

Figure 1:
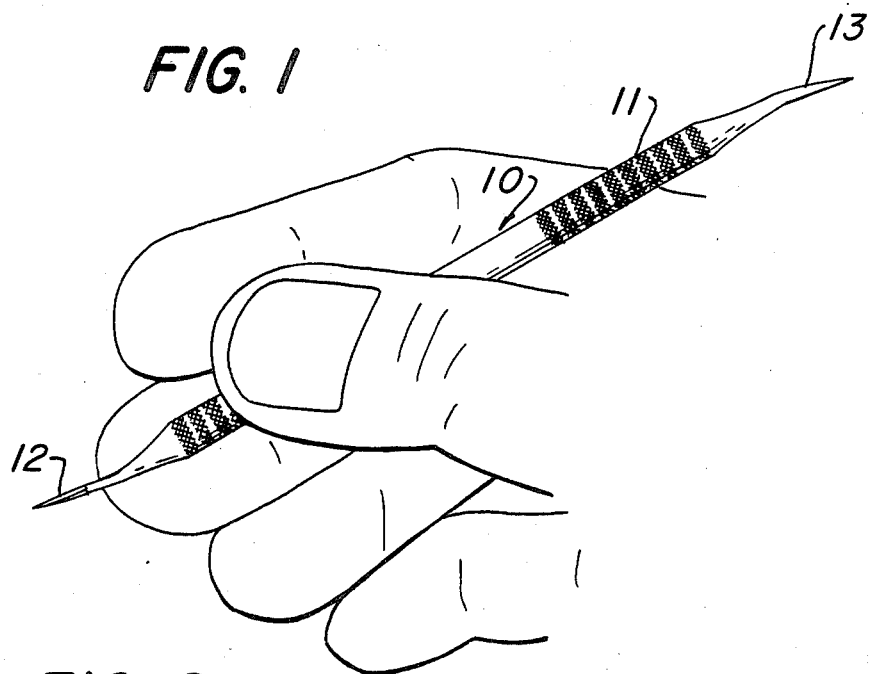
FIG. 1 is a perspective view of the instrument of this invention shown in a hand-held mode in position for carving.

The instrument shown generally as 10 in FIG. 1 is formed from a single metal block; however, those skilled in the art will appreciate that the shaft, shank and blade segments may also be formed individually as discrete elements and these may be joined together by known means to form a tool which is otherwise identical to that shown in FIGS. 1-5.

FIG. 1 shows the instrument in the hand of a user as it is intended to be held for engagement with a tooth surface. The handle 11 is milled to afford a pattern which provides enhanced gripping capabilities.

Figure 2:
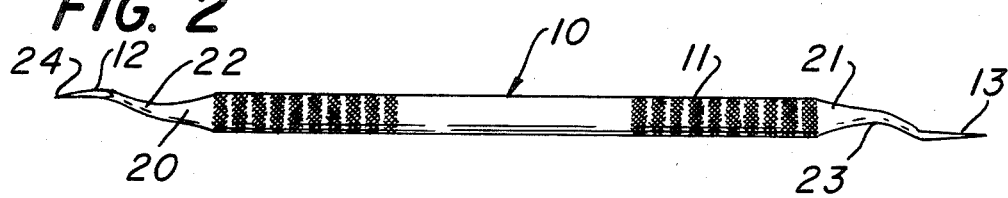
FIG. 2 is a side elevational view of the instrument shown in FIG. 1 rotated counterclockwise to reveal the concave configuration of the shank segments.
Figure 3:
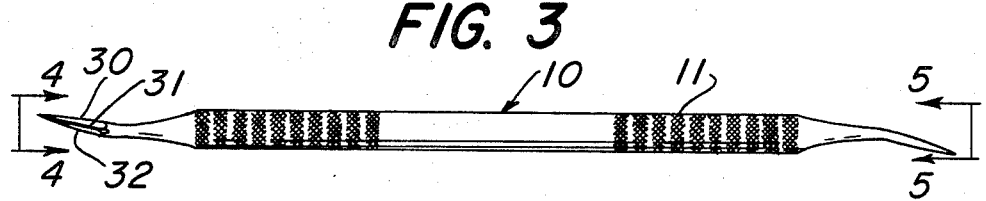
FIG. 3 is a side elevational view of the instrument shown in FIG. 1.

FIGS. 2 and 3 illustrate the oblique concavity of shank segments 20 and 21 and the disposition of blade segments 12 and 13. FIG. 2 shows only the cutting edges for blade 12 but shank 21 terminates in an identical blade having identical cutting edges and the absence of the latter from the figures is due solely to limitations in the Drawings and the orientation therein of the shown instrument. Accordingly, any description in this specification of shank 20 and blade 12 should be interpreted as a description also of shank 21 and blade 13 because these segments are in all respects identical.

The concavity 22 in shank segment 20 is designed to accept the user's middle finger and it lies about midway of the axial line between shaft 10 and tip 23 of blade segment 22. The concavity 23 in shank 21 is identical and it allows the user to employ either end of the instrument with equal facility.

The blade 12 is dually faceted to provide the cutting edges identified as 30, 31 and 32 in FIG. 3. This plurality of cutting edges constitutes an advance in the art because it provides the operator with an additional edge not available in known devices; moreover, each blade may be used to perform all phases of the restoration process. Blade 13 is identically constructed but, as noted above, its cutting edges are not visible due to the orientation of handle 11.

Figures 4, 5:
FIG. 4 is an end view of the instrument shown in FIG. 3 viewed along line 4—4.
FIG. 5 is an end view of the instrument shown in FIG. 3 viewed along line 5—5.

FIGS. 4 and 5 show the disposition of the blade segments 12 and 13 with respect to handle 11. The axial line of said handle passes through shank 20 above the concavity 22 on a line adjacent to tip 23. The faces of cutting edges 30, 31 and 32 are at essentially right angles to one another and they terminate in a tip 24 which fits into the interproximal spaces between the teeth for the removal of debris or stains in the buccal, lingual and cervical areas.

The instrument of this invention is employed by using a portion of the tooth which is being operated upon as a guide for the cutting edge while simultaneously bringing the underside of blade 12 into slidable contact with an area of an adjacent tooth. Accordingly, blade 22 serves as a guide by engaging the tooth in advance of the cutting edge so that the instrument can be easily manipulated.

In practice, the instrument 10 is employed by placing the tip of the middle finger within concavity 22 and cradling the handle 11 between the thumb and index finger as shown in FIG. 1. This disposition of the handle places blade 11 on a plane intersected by the exerted pressure of the operator so that maximum force can be applied to the tooth which is being operated upon.

When stains and deposits from palatal areas and tissue surfaces are to be removed from the lingual or buccal areas it is preferred to use the cutting edge which lies at the base of the curved shank, that is, the cutting edge identified as 31 in FIG. 3.

On the other hand, the contouring of the facial, mesial and distal surfaces is most effectively achieved by using the cutting edges identified as 30 and 32.

From the foregoing it is apparent that the multi-edged blade of this invention allows the operator to choose the cutting edge which is most appropriate for that quadrant of the mouth or dental plate which is sought to be restored and, therefore, it eliminates the need for a variety of instruments with different cutting edges.

This invention has been described by reference to precise embodiments but it will be appreciated by those skilled in the art that this invention is subject to modification and to the extent that those modifications would be obvious to one of ordinary skill they are within the scope of the appended claims.

What is claimed is:

1. A rigid dental instrument used for carving and cleaning teeth and plaster and stone dental casts which comprises:
   (1) an elongated handle which can be held and manipulated by a user;
   (2) an obliquely disposed first shank which is secured to one end of said handle including a curved inside segment which terminates in a first blade comprised of three linear cutting edges;
   (3) an obliquely disposed second shank which is secured to the opposite end of said handle including a curved inside segment which terminates in a second blade comprised of three linear cutting edges;
   (4) said first and second blades being comprised of two surfaces which form an angle of from about 40 to 50 degrees, each surface terminating in a cutting edge suitable for dental carving and leading to a pointed tip; and
   (5) said first and second blades having a third cutting edge which extends to the point of curvature on the inside portion of said shank immediately above said surface, said cutting edge conforming essentially to the surface of the tooth which is to be operated upon.

2. The dental instrument according to claim 1 wherein said first and second shanks obtrude from said handle to form a slightly spiraled concave segment for receiving the operator's middle finger.

3. The dental instrument according to claim 2 wherein said concave segment provides a fulcrum point upon which said instrument may turn when pressure is exerted.

4. The dental instrument according to claim 2 wherein the axial line of said handle extends beyond said concave segment on a line adjacent to the tip of said blade.

5. A method for restoring teeth and dental casts which comprises carving the proximal ridges and the facial, mesial, lingual and distal surfaces of said teeth and said casts with a rigid dental instrument comprising:
   (1) an elongated handle which can be held and manipulated by a user;
   (2) an obliquely disposed first shank which is secured to one end of said handle including a curved inside segment which terminates in a first blade comprised of three linear cutting edges;
   (3) an obliquely disposed second shank which is secured to the opposite end of said handle including a curved inside segment which terminates in a second blade comprises of three linear cutting edges;
   (4) said first and second blades being comprised of two surfaces which form an angle of from about 40–50 degrees, each surface terminating in a cutting edge suitable for dental carving and leading to a pointed tip; and
   (5) said first and second blades having a third cutting edge which extends to the point of curvature on the inside portion of said shank immediately above said surfaces, said cutting edge conforming essentially to the surface of the tooth which is to be operated upon.

6. The method according to claim 5 wherein restoration is effected by bringing the underside of said blade into slidable contact with an area of the tooth which is not being operated upon to provide guide means for said instrument.

7. The method according to claim 5 wherein the third cutting edge on said first blade and said second blade are used to clean stains and deposits from tissue surfaces and palatal, lingual and buccal areas.

* * * * *